United States Patent [19]

Kubo et al.

[11] Patent Number: 4,760,195

[45] Date of Patent: Jul. 26, 1988

[54] METHOD FOR PRODUCING A 5-BROMO-1-PENTANAL COMPOUND OR AN ACETAL DERIVATIVE THEREOF

[75] Inventors: Masaaki Kubo, Sayama; Kazuhiro Okura, Kawagoe, both of Japan

[73] Assignee: Kawaken Fine Chemicals Co., Ltd., Tokyo, Japan

[21] Appl. No.: 78,825

[22] Filed: Jul. 28, 1987

[51] Int. Cl.[4] .................. C07C 45/63; C07C 47/14
[52] U.S. Cl. ............................................ 568/466
[58] Field of Search ............................... 568/466

[56] References Cited

U.S. PATENT DOCUMENTS 3,109,865 11/1963 Foreman ........................ 568/466
3,940,445 2/1976 Reif et al. ...................... 568/466

FOREIGN PATENT DOCUMENTS 95233 6/1984 Japan ............................ 568/466

OTHER PUBLICATIONS

Koho et al. "Chemical Abstracts", vol. 101, p. 170707g (1984).
M. Akltar et al., J. Am. Chem. Soc., 87, 1807(1965).
J. F. Le Borgne, J. Organomet. Chem., 122, 123(1976).
W. Oppolzer et al., Helv. Chem. Acta., 60, 1801(1977).
R. Daniel Little et al., J. Org. Chem., 47, 362(1982).
Kuehne et al., J. Org. Chem., 43, 3705(1978).

*Primary Examiner*—Werren B. Lone
*Attorney, Agent, or Firm*—McAulay, Fields, Fisher, Goldstein & Nissen

[57] ABSTRACT

A 5-bromo-1-pentanal compound of the formula (I):

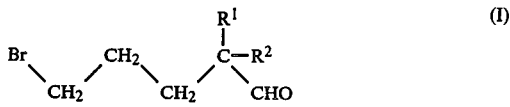

wherein $R^1$ and $R^2$ respectively represent, independently from each other, a member selected from the group consisting of a hydrogen atom and alkyl radicals having 1 to 7 carbon atoms, or an acetal derivative of said 5-bromo-1-pentanal compound, is produced by subjecting a starting compound selected from the group consisting of 4-pentenal compounds of the formula (II):

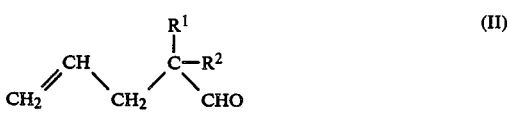

wherein $R^1$ and $R^2$ are as defined above, and acetal derivatives of the above-mentioned compounds, to a free radical addition reaction with hydrogen bromide in a liquid medium at a temperature of 10° C. to 60° C.; in the presence of a free radical initiator or by irradiating ultraviolet rays to the reaction mixture, and by collecting the resultant reaction product from the reaction mixture.

11 Claims, No Drawings

METHOD FOR PRODUCING A 5-BROMO-1-PENTANAL COMPOUND OR AN ACETAL DERIVATIVE THEREOF

BACKGROUND OF THE INVENTION (1) Field of the Invention

The present invention relates to a method for producing a 5-bromo-1-pentanal compound or an acetal derivative thereof.

More particularly, the present invention relates to a method for producing a 5-bromo-1-pentanal compound or an acetal derivative thereof from a corresponding 4-pentenal compound or an acetal derivative thereof, without decomposing or modifying the formyl or formyl acetal radical in the pentenal compound.

The 5-bromo-1-pentanal compound or the acetal derivative thereof has a backbone chain having five carbon atoms, a terminal of the chain consisting of a bromine atom and an opposite terminal of the chain consisting of an aldehyde or acetal, and thus is a bi-functional compound. Therefore, this compound is very useful as a molecular backbone chain-forming element when a physiologically active compound, for example, an indole alkaloid or a tri-cyclic sesquiterpen, is synthesized.

(2) Description of the Related Arts

It is known that a 5-bromo-1-pentanal compound can be produced by the following conventional methods.

(A) M. Akhtar et al., J. Am. Chem. Soc., 87, 1807 (1965) discloses a method of producing a 5-bromo-1-pentanal compound by the ring cleavage and bromination reaction of a cyclopentanol compound.

(B) J. F. Le Borgne, J. Organomet, Chem., 122, 123 (1976) discloses a method of producing a 5-bromo-1-pentanal compound by the alkylation of a corresponding aldimine compound with a dibromo-alkane.

(C) W. Oppolzer et al., Helv. Chem. Acta., 60, 1801 (1977) discloses a hydroboration of a 2-substituted-4-pentenal compound to produce a 5-bromo-1-pentanal compound.

(D) R. Daniel Little et al., J. Org. Chem., 47, 362 (1982) discloses a process for producing a 5-bromo-1-pentanal compound by partially reducing a corresponding 5-bromovaleronitrile and by hydrolyzing the partially reduced compound.

(E) M. E. Kuehne et al., J. Org. Chem., 43 3705 (1978) discloses a production of a 5-bromo-1-pentanal compound by reducing a corresponding 5,5-dimethoxyvaleric acid methylate, by converting the reduced product to the mesityl derivative thereof and then substituting the mesityl derivative with a bromine atom.

The above-mentioned methods (A) and (B) are disadvantageous in that the yield of the aimed compound is unsatisfactorily low, and thus is not suitable for industrial use.

The above-mentioned methods (C), (D), and (E) are disadvantageous in that an expensive compound such as diborane, butylaluminum hydride or lithium bromide must be used, and when the above-mentioned compound is used in a large amount, performance of these methods becomes increasingly dangerous, and thus they are not always usable for industrial purposes.

Generally, it is known that an aliphatic compound having a molecular terminal thereof consisting of a bromine atom can be produced by the anti-Markownikoff reaction of a corresponding aliphatic compound having a molecular terminal thereof consisting of a $CH_2=CH$-bond. However, the anti-Markownikoff reaction between an aliphatic compound having a molecular terminal thereof consisting of a $CH_2=CH$-bond and an opposite molecular terminal thereof consisting of a formyl radical (—CHO) and hydrogen bromide was not known before the present invention.

When the anti-Markownikoff reaction is applied to an aliphatic compound having the molecular terminal thereof consisting of a $CH_2=CH$-bond and the opposite terminal thereof consisting of a formyl radical, under usual reaction conditions, it was believed that the formyl radicals will release proton therefrom and be easily converted to carbonyl radicals. The resultant proton serves as a chain transfer agent and will cause undesirable other side-reactions to occur, and these side-reactions will result in a low yield of the aimed 5-bromo-1-pentanal compound or acetal derivative thereof.

Under the above-mentioned circumstance, there is a strong demand for a new method which can produce a 5-bromo-1-pentanal compound or the acetal derivative thereof at a high yield.

SUMMARY OF THE INVENTION

An object of the present invention is to provide a method for producing a 5-bromo-1-pentanal compound or an acetal derivative thereof at a satisfactorily high yield and at a low cost.

Another object of the present invention is to provide a method for producing a 5-bromo-1-pentanal compound or an acetal derivative thereof from a starting compound consisting of a corresponding 4-pentenal compound or an acetal derivative thereof at a high yield without decomposing or modifying a formyl radical in the starting compound.

The above-mentioned objects can be attained by the method of the present invention in which a 5-bromo-1-pentanal compound of the formula (I):

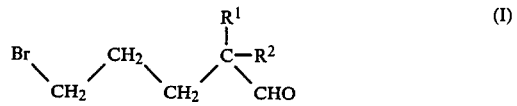

wherein $R^1$ and $R^2$ respectively represent, independently from each other, a member selected from the group consisting of a hydrogen atom and alkyl radicals having 1 to 7 carbon atoms, or an acetal derivative of said 5-bromo-1-pentanal compound, is produced by the steps of:

subjecting a reaction mixture containing hydrogen bromide and a starting compound selected from the group consisting of 4-pentenal compounds of the formula (II):

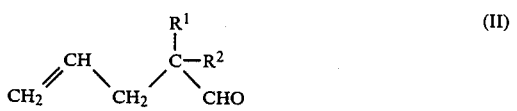

wherein $R^1$ and $R^2$ are as defined above, and acetal derivatives of the above-mentioned 4-pentenal compounds, dissolved in a liquid medium to a free radical addition reaction at a temperature of 10° C. to 60° C.; and collecting the resultant reaction product from the reaction mixture.

The above-mentioned free radical addition reaction of the starting compound hydrogen bromide can be effected in the presence of a free radical initiator consisting of at least one free radical initiating azo compound.

Alternatively, the free radical addition reaction can be effected by irradiating actinic rays, for example, ultraviolet rays, to the reaction mixture containing the starting compound and hydrogen bromide in the liquid medium.

DESCRIPTION OF THE PREFERRED EMBODIMENTS

In the process of the present invention, a starting compound (a feed) consists of a member selected from 4-pentenal compounds of the formula (II) which can be indicated as follows:

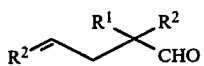

wherein $R^1$ and $R^2$ respectively represent, independently from each other, a hydrogen atom or an alkyl radical having 1 to 7 carbon atoms, and acetal derivatives of the above-mentioned 4-pentenal compound.

The 4-pentenal compound usable for the method of the present invention is preferably selected from 4-pentenal, 2-ethyl-4-pentenal, 2,2-dimethyl-4-pentenal, 2-butyl-2-ethyl-4-pentenal and 2-butyl-4-pentenal and acetal derivatives of the above-mentioned compounds.

The acetal derivatives usable for the method of the present invention can be selected from, for example, lower alkyl acetal derivatives, for example, 1,1-dimethoxy-2-ethyl-4-pentene and 1,1-diisopropoxy2-ethyl-4-pentene and cyclic acetal derivatives, for example, 2,2-dimethyl-4-pentenalethyleneacetal, 2-butyl-2-ethyl-4-pentenal-2,2-dimethyl-1,3-propyleneacetal, and 2-ethyl-4-pentenal-1,3-propyleneacetal. The cyclic acetal derivatives include multi-cyclic acetyl derivatives, for example, 3,9-bis(1-ethyl-3-butenyl)2,4,8,10-tetraoxaspyro[5,5]undecane.

In the free radical addition reaction in the method of the present invention, hydrogen bromide molecules in the reaction mixture must be converted to free bromine radicals which are attached to the 5-position of the 4-pentenal compound in accordance with the anti-Markownikoff addition reaction as follows.

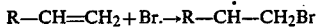

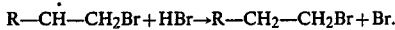

Wherein R represents a —CH$_2$C(R$^1$R$^2$)—CHO group.

As is clear from the above reactions, after the free bromine radials are generated from the hydrogen bromide molecules, the bromine radials serve as a chain transfer agent and the addition of the free bromine radicals to the 5-position of the 4-pentenal compound is carried out in accordance with a chain transfer reaction.

In the free radical addition reaction of the 4-pentenal compound with the hydrogen bromide, the formyl radical (—CHO) in the 4-pentenal compound releases proton therefrom and, sometimes, is modified by an undesirable side reaction.

Accordingly, in the method of the present invention, the modification of the formyl radical by the side reaction is prevented. To this end, in the method of the present invention, the rate of generation of the free radicals is controlled to a relatively low level by restricting the reaction temperature to the range of from 10° C. to 60° C.

In the method of the present invention, the free radical addition reaction of the starting compound with hydrogen bromide is preferably effected in the presence of a free radical initiator consisting of at least one free radical-initiating azo compound. The free radical initiator is preferably used in a relatively small amount of from 0.01% to 1%, more preferably, from 0.1% to 1%, based on the weight of the feed consisting of a 4-pentenal compound of the formula (II) or an acetal derivative thereof.

The use of the small amount of free radical initiator is effective for preventing the modification of the formyl radical in the starting 4-pentenal compound.

The azo compound usable for the method of the present invention must be selected from those which are chemically stable over a long period of storage and are capable of causing hydrogen bromide molecules in a liquid reaction medium to be converted to free bromine radicals at the reaction temperature of from 10° C. to 60° C., at a high efficiency.

For this purpose, the free radical-initiating azo compound is preferably selected from 2,2'-azobisisobutyronitrile, 1,1'-azo-bis(cyclohexane-1-carbonitrile), 2,2'-azo-bis(2,4-dimethylvaleronitrile) and 2,2'-azobis(4-methoxy-2,4-dimethylvaleronitrile). The most preferable azo compound is 2,2'-azobisisobutyronitrile.

In another embodiment of the method of the present invention, the free radical addition reaction is effected by irradiating actinic rays to the reaction mixture containing the starting compound and hydrogen bromide dissolved in a liquid reaction medium.

The actinic ray radiation must impart the necessary energy to the hydrogen bromide molecules to be converted to free bromine radicals. For this purpose, preferably the actinic rays are ultraviolet rays, more preferably near-ultraviolet rays, in a wave length band of from about 800 nm to 250 nm. The near-ultraviolet rays are irradiated from a low pressure mercury lamp at a high efficiency. The actinic rays may be irradiated from other lamps, for example, a sunlamp or tungsten lamp.

The amount of the actinic rays to be irradiated to the reaction mixture should be controlled to an extent such that the formyl radical in the starting 4-pentenal compound is not modified.

In the method of the present invention, usually the hydrogen bromide is used in an amount of 1 to 2 equivalents per equivalent amount of the feed.

In the method of the present invention, the reaction of the starting compound and the hydrogen bromide is carried out in a liquid medium, which is preferably not active (inert) to the reaction of the present invention, volatile, and non-polar. Usually, the liquid medium consists of at least one inert, volatile, non-polar hydrocarbon selected from, for example, n-hexane, n-heptane and cyclohexane which preferably have a boiling point of 120° C. or less.

The liquid reaction medium is preferably used in an amount of from 2 to 20 times, more preferably 5 to 10 times, by weight of the feed.

The free radical addition reaction of the starting compound with hydrogen bromide in accordance with the present invention is carried out at a temperature of 10° C. to 60° C., preferably 15° C. to 45° C., while stirring the reaction mixture. That is, usually, a hydrogen bromide gas is blown into a solution of the starting compound in the liquid reaction medium in the presence of the specific free radical initiator or under an irradiation of actinic rays to the reaction mixture, at the above-mentioned specific temperature.

A reaction temperature of more than 60° C. will cause undesirable side-reactions to occur in the reaction mixture, and these side-reactions will reduce the yield of the aimed compound. When the reaction is carried out at a temperature of less than 10° C., the free radical addition reaction proceeds at a unsatisfactorily low reaction velocity.

In accordance with the process of the present invention, a 5-bromo-1-pentanal compound or an acetal derivative thereof is produced at a high yield. The 5-bromo-1-pentanal compounds capable of being produced by the method of the present invention include, for example, 5-bromo-2-ethyl-1-pentanal, 5-bromo-2,2-dimethyl-1-pentanal, 5-bromo-2-butyl-2-ethyl-1-pentanal and 5-bromo-2-butyl-1-pentanal.

The above-mentioned 5-bromo-1-pentanal compounds may be in the form of an acetal derivative thereof.

When a starting compound consisting of a 4-pentenal compound of the formula (I) is subjected to the method of the present invention, the resultant compound is a 5-bromo-1-pentanal compound of the formula (II).

Also, when the method of the present invention is applied to a starting compound consisting of an acetal derivative of a 4-pentenal compound of the formula (I), a portion of the acetal groups in the acetal derivative molecules is decomposed and converted to formyl groups, by a side reaction of the free radical addition reaction, and therefore, the resultant reaction product consists of a mixture of 5-bromo-1-pentanal compound of the formula (II) and an acetal derivative thereof. The acetal derivative in the resultant mixture can be converted to the corresponding 5-bromo-1-pentanal compound by subjecting the mixture to a hydrolysis procedure. Also, the 5-bromo-1-pentanal compound contained in the resultant reaction mixture can be converted to the corresponding acetal derivative thereof by applying to the mixture an acetal-forming procedure with an acetal-forming alcohol compound.

After the free radical addition reaction is completed, the resultant reaction product is collected from the reaction mixture by recovering the liquid medium and the residual hydrogen bromide by evaporation.

Where the starting compound consisting of an acetal derivative of a 4-pentenal compound is used, the resultant acetal derivative of the 5-bromo-1-pentanal compound is treated with a diluted aqueous solution of an acid, for example, hydrochloric acid, at an elevated temperature, for example, 30° C. to 80° C., to convert it to a corresponding 5-bromo-1-pentanal compound. The acid aqueous solution phase is then removed from the treated mixture, and the residual reaction mixture is neutralized with an alkali aqueous solution to separate a resultant organic phase from an inorganic aqueous phase, the resultant organic phase is collected from the reaction mixture, and the liquid medium and the residual hydrogen bromide are evaporated from collected organic phase.

In the process of the present invention, the formyl radical in the starting compound is maintained in a non-decomposed or non-modified state, the formation of undesirable free radicals is restricted, and therefore, the aimed compound can be obtained at a high yield.

Generally, in the method of the present invention, a hydrogen bromide gas is blown into a solution of the starting compound and the free radical initiator dissolved in the inert, non-polar liquid medium or into a solution of the starting compound dissolved in the inert, non-polar liquid medium while irradiating actinic rays to the resultant reaction mixture, at a temperature of from 10° C. to 60° C.

The present invention will be further illustrated by the following examples.

EXAMPLE 1

A three-necked flask having a capacity of 300 ml was equipped with a thermometer, a reflux condenser connected to a tube for washing a gas produced in the flask with an alkali aqueous solution, and a conduit connected to a supply source of a hydrogen bromide gas. The flask was first charged with 5.6 g of a starting compound consisting of 2-ethyl-4-pentenal and 200 ml of n-heptane and then with 16.8 mg of 2,2'-azobisisobutyronitrile. The resultant mixture was admixed with the hydrogen bromide gas blown into the flask, in an amount of two times the molar amount of the starting compound over a period of 2 hours while the resultant reaction mixture was maintained at a temperature of from 38° C. to 40° C. and was stirred. Thereafter, the resultant reaction mixture was neutralized with an aqueous solution of sodium carbonate and was washed with water. The washed reaction mixture was subjected to a distillation procedure under a reduced pressure to recover n-heptane from the reaction mixture. Another distillation procedure under a reduced pressure was further applied to the reaction mixture to remove the residual n-heptane and non-reacted hydrogen bromide. A colorless clear liquid consisting of 5-bromo-2-ethyl-1-pentanal was obtained in an amount of 6.1 g and at a yield of 63%.

EXAMPLE 2

The same reactor as that mentioned in Example 1 was first charged with 31.2 g of 2-ethyl-4-pentenal ethyleneacetal and 200 ml of n-heptane, and then with 31.2 mg of 2,2'-azobisisobutyronitrile. A hydrogen bromide gas was blown in an amount of 1.3 times the molar amount of the starting compound into the resultant mixture. The reaction was carried out over a period of 4.7 hours in the same manner as that mentioned in Example 1.

The resultant reaction mixture was subjected to a GLC (gas-liquid chromatography) analysis. It was found that a portion of the resultant pentanal acetal compound was converted to the corresponding pentanal compound and the resultant pentanal compound fraction and non-converted pentanal acetal compound fraction were in a molar mix ratio of about 1:2.

The reaction product was treated with 6.2 g of ethylene glycol to convert the pentanal compound fraction to the corresponding acetal derivative thereof.

The reaction mixture was neutralized with a sodium carbonate aqueous solution, was washed with water, and then subjected to a distillation procedure under a reduced pressure. A colorless clear liquid consisting of 5-bromo-2-ethyl-1-pentanal ethylene acetal was obtained in an amount of 37.9 g, corresponding to a yield of 79.9%.

EXAMPLES 3 to 7

In each of Examples 3 to 7, the same procedures as those described in Table 1 were carried out except that the type and amount of the starting compound as shown in Table 1 was mixed with the types and amounts of the liquid medium and the initiator as shown in Table 1, the hydrogen bromide gas was blown in the amount as shown in Table 1 into the mixture at the temperature shown in Table 1, and the type and amount of the resultant compound as shown in Table 1 was obtained in the yield as shown in Table 1.

was stirred for two hours at the temperature of from 18° C. to 20° C., while irradiating ultraviolet rays thereto.

Thereafter, the reaction mixture was transferred to a three necked flask having a capacity of 2000 ml and was treated with a hydrochloric acid aqueous solution to convert the resultant 5-bromo-1-pentanal acetal compound to the corresponding 5-bromo-1-pentanal compound. An organic phase was separated from an aqueous phase, the aqueous phase was removed, and the recovered organic phase was neutralized with a sodium carbonate aqueous solution, washed with water, and then distilled under a reduced pressure in the same

TABLE 1

| Example No. | Starting compound | | Liquid medium | | HBR (*1) (Equivalent) | AIBN (*2) (mg) | Reaction temperature (°C.) | Resultant product | | |
|---|---|---|---|---|---|---|---|---|---|---|
| | Compound | Amount (g) | Compound | Amount (ml) | | | | Compound | Amount (g) | Yield (%) |
| 3 | 2-ethyl-4-pentenal-1,2-propylene acetal | 51.0 | n-hexane | 300 | 2 | 48.6 | 38 to 40 | 5-bromo-2-ethyl-1-pentanal-1,2-propylene acetal | 64.5 | 85.7 |
| 4 | 3,9-bis(1-ethyl-3-butenyl)-2,4,8,10-tetraoxaspyrol[5,5]undecane | 46.8 | n-heptane | 300 | 2 | 48.6 | 38 to 45 | 3,9-bis(4-bromo-1-ethyl)-2,4,8,10-tetraoxaspyro 5,5 undecane | 61 | 87.4 |
| 5 | 2,2-dimethyl-4-pentenal ethylene acetal | 46.8 | n-heptane | 300 | 1.3 | 94.0 | 38 to 40 | 5-bromo-2,2-dimethyl-1-pentanel ethylene acetal | 42.2 | 90.2 |
| 6 | 2-butyl-2-ethyl-4-pentenal-2,2-dimethyl propylene acetal | 50.8 | Cyclohexane | 300 | 2 | 50.0 | 40 to 42 | 5-bromo-2-butyl-2-ethyl-1-pentanal-2,2-dimethyl propylene acetal | 58.5 | 87.3 |
| 7 | 2-butyl-4-pentenal ethylene acetal | 13.8 | n-heptane | 250 | 1.7 | 40.0 | 30 to 35 | 5-bromo-2-butylene-1-pentanal ethylene acetal | 19.0 | 95.7 |

Note:
(*1) Amount of HBr in equivalent based on the equivalent amount of feed
(*2) 2,2'-Azobisisobutyronitrile.

EXAMPLE 8

A three necked flask having a capacity of 500 ml was equipped with a low pressure mercury lamp located in the center portion of the flask, with a reflux condenser connected to a tube for washing a gas generated in the flask with an alkali aqueous solution, with a thermometer, and with a conduit connected to a supply source of a hydrogen bromide gas.

The flask was charged with 11.2 g of 2-ethyl-4-pentenal and 400 ml of n-heptane. The reaction mixture in the flask was irradiated by ultraviolet rays having a wave length band of from 300 nm to 250 nm from the low pressure mercury lamp at a temperature of 18° C. to 20° C. over a period of 4 hours while a hydrogen bromide gas was blown in a molar amount of 2 times that of the starting compound into the reaction mixture in the flask and the reaction mixture was stirred. The stirring operation was further carried out for one hour.

The resultant reaction mixture was treated in the same manner as that described in Example 1.

A colorless transparent liquid consisting of 5-bromo-2-ethyl-1-pentanal was obtained in an amount of 15.2 g and in a yield of 78.9%.

EXAMPLE 9

The same procedures as those described in Example 8 were carried out with the following exception.

The starting material consisting of 31.2 g of 2-ethyl-4-pentenal ethylene acetal was dissolved in 400 ml of n-heptane in the flask. After the blowing of the hydrogen bromide gas was completed, the reaction mixture manner as that mentioned in Example 1.

A colorless transparent liquid consisting of 5-bromo-2-ethyl-1-pentanal was obtained in an amount of 36.2 g and in a yield of 93.7%.

EXAMPLE 10

The same procedures as those described in example 8 were carried out with the following exception.

The starting compound consisting of 47.4 g of 2-ethyl-4-pentenal dimethyl acetal was dissolved in 300 ml of n-heptane. The irradiation of ultraviolet rays from the low pressure mercury lamp was carried out over a period of 3 hours, while the hydrogen bromide gas was blown in a molar amount of three times that of the starting compound into the starting compound solution at a temperature of 20° to 25° C. and while the reaction mixture was stirred. The stirring operation was continued for a further period of 3 hours while irradiating ultraviolet rays thereto. Then, the reaction mixture was admixed with 100 ml of methyl alcohol and the admixture was stirred at room temperature for 12 hours.

A colorless transparent liquid consisting of 5-bromo-2-ethyl-1-pentanal dimethylacetal was obtained in an amount of 24.3 g and in a yield of 51.3%.

COMPARATIVE EXAMPLE 1

The same procedures as those described in Example 2 were carried out except that the reaction was carried out at a temperature of 70° C. to 75° C. over a period of 5 hours.

The resultant product was a light brownish clear liquid containing 5-bromo-2-ethyl-1-pentanal ethylene acetal in an amount of 27.65 g and at an yield of 58.3%.

As a result of the GLC analysis, it was found that the purity of the 5-bromo-2-ethyl-1-pentanal ethylene acetal in the light brownish clear liquid was 78.2%.

COMPARATIVE EXAMPLE 2

The same procedures as those described in Comparative Example 1 were carried out except that the hydrogen bromide gas was blown into the 2-ethyl-4-pentenal ethylene acetal-containing mixture at a temperature of 2° C. to 8° C. and the resultant reaction mixture was maintained at the above-mentioned temperature in the same manner as that mentioned in Example 2.

In the hydrogen bromide-blowing procedure, it was found that a white solid complex substance was deposited in the gas-blowing entrance portion of the reaction flask, and thus the gas-blowing procedure was restricted.

The resultant reaction product was a colorless clear liquid containing 5-bromo-2-ethylpentanal ethylene acetal in a small amount of 19.9 g at a very low yield of 31.5%.

We claim:

1. A method for producing a 5-bromo-1-pentanal compound of the formula (I):

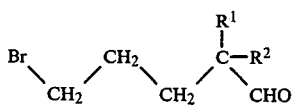 (I)

wherein $R^1$ and $R^2$ respectively represent, independently from each other, a member selected from the group consisting of a hydrogen atom and alkyl radicals having 1 to 7 carbon atoms, or an acetal derivative of said 5-bromo-1-pentanal compound, comprising the steps of:

subjecting a reaction mixture containing hydrogen bromide and a starting compound selected from the group consisting of 4-pentenal compounds of the formula (II):

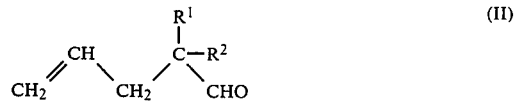 (II)

wherein $R^1$ and $R^2$ are as defined above, or acetal derivatives of said 4-pentenal compounds dissolved in a liquid medium, to a free radical addition reaction at a temperature of 10° C. to 60° C.; and, collecting the resultant reaction product from the reaction mixture.

2. The method as claimed in claim 1, wherein the free radical addition reaction is effected in the presence of a free radical initiator consisting of at least one free radical-initiating azo compound.

3. The method as claimed in claim 2, wherein the free radical initiator is in an amount of 0.01% to 1% based on the weight of the starting compound.

4. The method as claimed in claim 2, wherein the free radical-initiating azo compound is selected from the group consisting of 2,2'-azobisisobutyronitrile, 1,1'-azo-bis(cyclohexane-1-carbonitrile), 2,2'-azo-bis(2,4-dimethylvaleronitrile) and 2,2'-azo-bis(4-methoxy-2,4-dimethylvaleronitrile).

5. The method as claimed in claim 1, wherein the free radical addition reaction is effected by irradiating actinic rays to the reaction mixture.

6. The method as claimed in claim 5, wherein the actinic rays are ultraviolet rays.

7. The method as claimed in claim 5, wherein the actinic rays are near-ultraviolet rays irradiated from a low pressure mercury lamp.

8. The method as claimed in claim 1, wherein the liquid medium comprises at least one inert hydrocarbon selected from n-hexane, n-heptane, and cyclohexane.

9. The method as claimed in claim 1, wherein the liquid medium is in an amount of 2 to 10 times the weight of the starting compound.

10. The method as claimed in claim 1, wherein the hydrogen bromide is in an amount of 1 to 2 equivalent per equivalent amount of the starting compound.

11. The method as claimed in claim 1, wherein, in the collecting step, the liquid medium and the residual hydrogen bromide are recovered under a reduced pressure.

* * * * *